United States Patent [19]

Schirmer et al.

[11] Patent Number: 4,669,837

[45] Date of Patent: Jun. 2, 1987

[54] OPHTHALMOSCOPE WITH LASER PHOTOCOAGULATOR

[75] Inventors: Kurt E. Schirmer, 56 Granville Road, Hampstead, Quebec, Canada, H3X 3B6; Charles Munnerlyn, Sunnyvale, Calif.

[73] Assignee: Kurt E. Schirmer, Hampstead, Canada

[21] Appl. No.: 664,326

[22] Filed: Oct. 24, 1984

[51] Int. Cl.$^4$ .................. G02B 21/22; A61B 3/10
[52] U.S. Cl. .................... 351/221; 350/516; 351/205
[58] Field of Search ............ 351/205, 214, 221; 350/516

[56] References Cited

U.S. PATENT DOCUMENTS 4,015,898  4/1977  Schirmer ..................... 351/221
4,307,944  12/1981  Schirmer.

Primary Examiner—Rodney B. Bovernick
Attorney, Agent, or Firm—Schwartz, Jeffery, Schwaab, Mack, Blumenthal & Evans

[57] ABSTRACT

An ophthalmic microscope combined with a laser photocoagulator and a binocular comprising a first telescopic tubular section connected to the binocular and a second tubular section slideably connected to the first section. The second section comprises an objective lens and a first reticle fixed to the second telescope section spaced within the telescope. A second reticle means is provided on the first telescopic section between the objective lens and the first reticle. A field lens is provided within the first telescopic section and is arranged such that the focal point of the field lens coincides with the second reticle. Laser means includes means on the first telescopic section for passing the laser beam into the telescope along an axis contained within the plane which includes the second reticle. The binocular comprises a field lens, a pair of object lenses on either side of the optical axis between the field lens and the binocular and is adapted to erect the image and is adapted to separate rays to the left eye and to the right eye. A first rhomboid prism is adapted to divert the rays from one side to the other and a second rhomboid prism is adapted to divert the rays to the other side to avoid pseudostereopsis.

7 Claims, 3 Drawing Figures

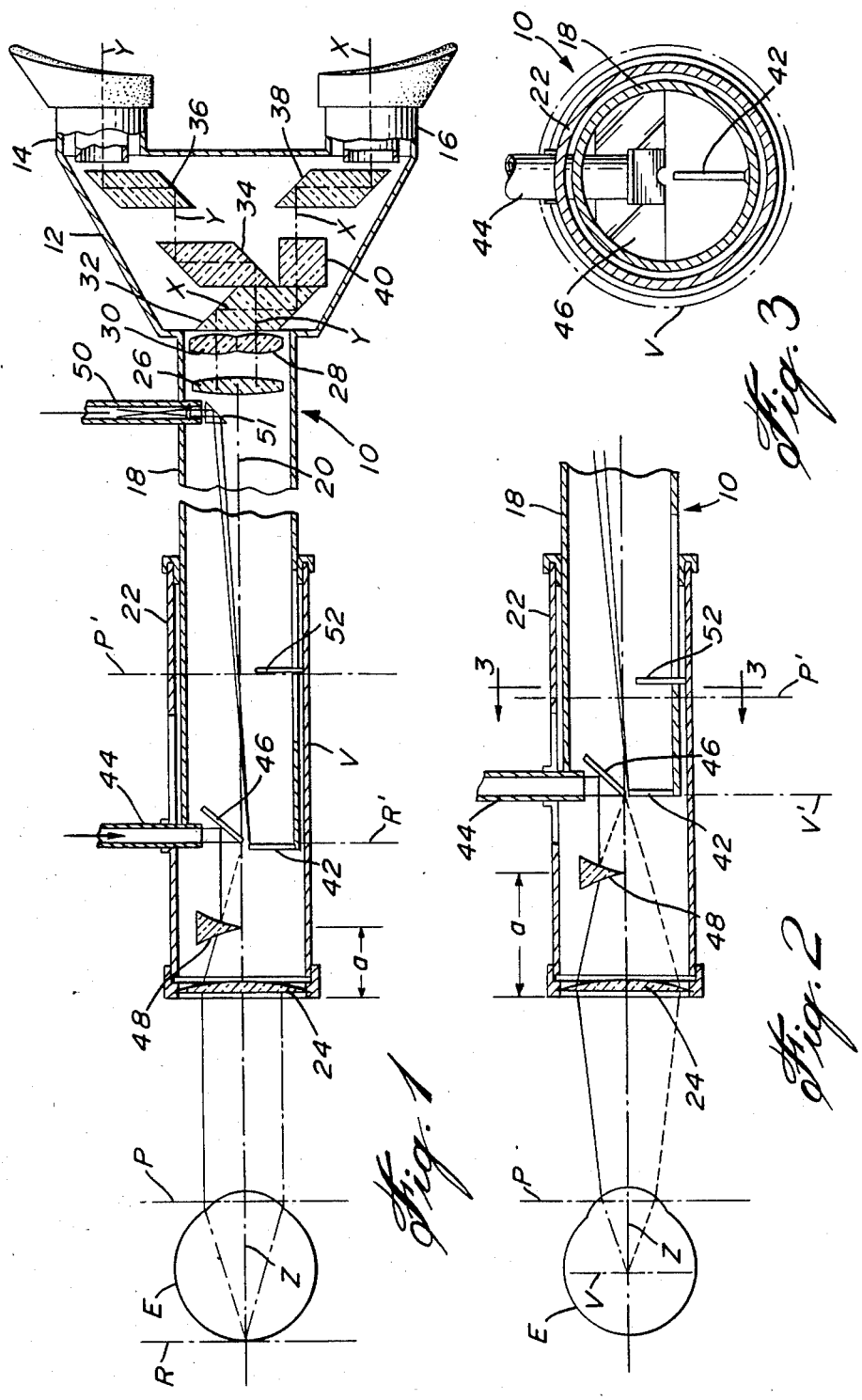

OPHTHALMOSCOPE WITH LASER PHOTOCOAGULATOR

BACKGROUND OF THE INVENTION

1. Field of the Invention

The present invention relates to an ophthalmic microscope, and more particularly, to an ophthalmic microscope provided with a laser photocoagulator with a system for ranging the focal point of the laser beam, and still further there is provided an improved binocular having microscopic magnification with erect, wide field, stereoscopic image viewing.

2. Description of the Prior Art

There are several laser photocoagulators used presently for cutting within the vitreous and for the purpose of fusing a detached retina. YAG lasers are also used for cutting strands or membranes which might develop in the pupil of the eye as well as in the vitreous cavity, that is, spaced from the fundus.

The problem with cutting strands in the vitreous cavity is that care must be taken to ensure the safety of the retina. For this purpose, the greatest possible aperture of beam is required which ensures the smallest possible focal spot with the shortest depth of focus of the laser beam.

The presently used system of a focal microscope which utilizes a plano concave contact lens, results in a diminished aperture angle. The pupil acts as a field stop and narrows the field for the observer. The alternative is to complicate the YAG beam delivery system to an extremely wide angle by space occupying devices on the slit lamp microscope that diminish the mobility of the device, or to use convex concave contact lenses that increase the beam aperture angle which compromises the field for the observer and further compromises stereopsis.

To overcome these difficulties, slit lamp illumination microscopy was described in the U.S. Pat. No. 4,307,944, Kurt Schirmer, issued Dec. 29, 1981. This patent described the use of an Argon laser photocoagulator but does not refer to the potential use of a YAG neodymium laser beam. The laser beam in the former patent came to a focus within the telescope. In the case of utilizing a YAG laser, the concept of focusing the laser beam within the telescope must be avoided.

Various erecting, stereoscopic binoculars are also known from the prior art. However, such prior art binoculars inevitably utilize hand-made expensive erecting prisms, such as roof top prisms.

SUMMARY OF THE INVENTION

It is an aim of the present invention to provide an improved fundus microscope for the purpose of improved fundus surgery, capable of being provided with high intensity laser with slit lamp illumination and improved aiming capabilities of the laser beam.

The device must provide a high luminosity image with the lowest possible flux of light input into the eye to avoid damage by illumination. The focus of the laser beam must be as small as possible to avoid damage outside the point of target.

It is also the aim of the present invention to provide an improved binocular with image erection of the inverted aerial image and with the greatest possible stereo disparity for a given size of patient pupil.

It is also an aim of the present invention to provide an improved binocular with erecting lens for stereoscopic viewing.

A construction in accordance with the present invention comprises a fundus microscope having a binocular, a first telescopic tubular section connected to the binocular, a second tubular section slidably connected to the first section, the second section comprising an objective lens and a first reticle fixed to the second telescope section spaced within the telescope, a second reticle means provided on the first telescope section between the objective lens and the first reticle, a field lens within the first telescopic section and arranged such that the focal point of the field lens coincides with the second reticle, illumination means adjacent the field lens and having a focal point coincident with said second reticle, laser means including means on said first telescopic section for passing the laser beam into the telescope along an axis contained within a plane which includes the second reticle, a reflecting mirror provided in the telescope above the optical axis of the telescope and adapted to deflect the laser beam towards said objective lens, an equiconcave lens provided on the first section between the mirror and the objective lens adapted to refract the laser beam passing to the objective lens and from the objective lens to the eye, the system being such that the fundus image of the eye is within the telescope and the focal point of the field lens at the second reticle in any part of the image of the eye corresponds with the object target within the eye.

The binocular in accordance with the present invention comprises a field lens, a pair of object lenses on either side of the optical axis between the field lens and the binocular adapted to erect the image and adapted to separate rays to the left eye and to the right eye, a first rhomboid prism adapted to divert the rays from one side to the other, and a second rhomboid prism adapted to divert the rays to the other side to avoid pseudostereopsis.

Thus, the present invention includes an ophthalmic microscope that is provided with a laser photocoagulator with a system for ranging the laser beam's focus. An improved binocular is provided with microscopic magnification that erects the image of the fundus oculi for the observer. It provides the viewer with microscopic magnification of the fundus image with a wide field. The large aperture of the objective lenses permits the viewing of an image of high luminosity with the lowest possible luminous flux of the illumination slit lamp device, so as to prevent damage to the retinal tissue by light during lengthy examinations, during surgery of retina or during vitrectomy. The stereoscopic efficiency of the binocular is as a result of the positioning of the pair of objective lenses with a large stereo base, considering their optical centers. The objective lenses are adjacent one another so that even a small pupil of the patient will provide stereoptic conditions for the observer. The optical combination of the stereoptic objectives adjacent one another provides a self-adjusting optical device to accommodate patient pupils of all sizes for stereoscopic viewing. The reduction of pupil size during surgery no longer forces to terminate surgery prematurely.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a schematic cross-sectional view of a typical ophthalmic microscope in accordance with the present invention;

FIG. 2 is a fragmentary view, similar to FIG. 1, showing the telescope portion in a different position; and FIG. 3 is a cross-sectional view taken along line 3—3 of FIG. 2.

DESCRIPTION OF THE PREFERRED EMBODIMENTS

Referring now to the drawings, there is shown, in relation to the eye of a patient E, an ophthalmic microscope 10 having a Keplerian stereo binocular 12 provided with oculars 14 and 16. A first telescopic section 18 is connected to the binocular 12 along the optical axis thereof. The optical axis is identified by the number 20. A second telescopic section 22, slideably mounted on the first section 18, includes at one end thereof an object lens 24.

The first telescopic section is provided with a field lens 26 and spaced closely thereto is a pair of objective lenses 28 and 30. The objective lenses 28 and 30 are object lenses for the binocular system. The field lens is spaced from the objective lens by a distance of 5 mm.

Within the binocular is found a rhomboid prism 32 which is arranged so as to divert the rays from left to right. The object lenses 28 and 30 will separate the rays passed through the field lens. These rays are identified X and Y. Prior to entering the rhomboid prism 32, ray X is viewed on the right-hand side of the binocular as it emits from the object lens 30 and is redirected as seen towards the left eye represented by the ocular 16. A further rhomboid prism 34 is provided adjacent the rhomboid prism 32 so as to redirect the ray Y towards the ocular 14.

Further rhomboid prisms 36 and 38, pivotable about the X and Y axes, provide for adjustable spacing of the rays and the oculars 14 and 16. In order that the rays X and Y travel the same distance both within a prism medium and through the air, a cube type prism 40 is shown adjacent the first rhomboid prism 32, allowing the ray X to pass therethrough to the rhomboid prism 38.

A pankratic zooming device may be built into the binocular. The addition of a beam splitting prism for a viewer or a camera may be provided by an outlet (not shown). The binocular can be inclined by 45° to the axis of the telescopic device. The incline by 45° aids the surgeon during vitrectomy in the posterior part of the vitreous. The incline of the ocular can be either stationary or adjustable from 0°–45° to accommodate working conditions.

The first telescope section 18 includes a reticle 42 at the end thereof. Immediately above the reticle 42 is a YAG neodymium laser beam directing tube 44 and a mirror 46 which is set at 45° to the axis of the tube 44. The tube 44 is mounted to the first telescope section 18. A one half equi-concave lens 48 is mounted to the first telescope section but spaced in front of the deflecting mirror 46, as shown in the drawings.

The device to convey the YAG neodymium laser beam of 1064 nanometers passes into the telescope. It is deflected by a mirror 46 from the perpendicular to an axis parallel to the axis of the telescope. The mirror 46 may be stationary and occupy only a part of the diameter of the section 18 or fill the same completely but be removable from the observer's field so that it is in place only when the YAG neodymium laser beam is used. A concave lens is used to diverge the parallel laser beam of 1064 nanometers to direct its ultimate focus to the point anterior to the retina that is coincident with the target reticle 42 within the telescope. This point is the virtual focal point for the concave lens 48. The concave lens remains in fixed distance with the mirror and the target reticle and in variable distance with the objective lens depending on the depth of the target on the Z axis in the vitreous.

The neodymium laser beam is directed by a helium neon targeting beam that is included in the light path of the YAG neodymium laser. The neodymium beam may be temporarily altered, i.e., by doubling its frequency and halving the wavelength whereby it becomes visible, for the purposes of targeting or photocoagulation. The targeting beam is shifted out of the light path of the YAG laser (or doubled in frequency) beam as the YAG laser beam's cutting action is engaged.

A slit lamp illumination system is illustrated at 50, and the beams of the slit lamp 50 are directed by mirror prism 51 to focus at the top of the reticle 42. The focal length of the field lens 26 also coincides with the top of the reticle 42. The axis of the slit lamp illumination projector is at right angles to the plane of the cross-section of the drawing so that the prism coincides with the valley between the objective lens 26 and 28.

The ophthalmic microscope of the present invention is an afocal system, and thus the rays emitting from the object lens 24, a convex lens, are directed parallel towards the eye E. Providing the target is on the retina, they will become convergent when the target is in the vitreous as shown in FIG. 2.

The second telescopic section 22 is also provided with a reticle 52 which is utilized to judge the position of the pupil in the image of the eye within the telescope and aid to avoid grazing the pupil with the laser. The reticle 42 is used for aiming the beam, both illumination and the laser beams, towards the eye. As is well known, the afocal optical system allows the optical system of the eye to be utilized, and thus the rays will be focused depending on the setting of the second telescopic section 22 relative to the first telescopic section 18, either on the fundus of the eye or at a point in the vitreous.

The one half equi-concave lens 48 and the object lens 24 are arranged such that the laser will focus at the intersection of the slit lamp beam with the optical axis. Thus, the reticle 42 is properly aimed along the optical axis to the point to be cut. The focus of the beam within the vitreous can be determined by the position of the reticle 42 within the image of the eye within the telescope. This will correspond to the exact point within the eye where the laser will be focused. If an object other than on the fundus but actually in the vitreous is required to be cut, the telescope section 22 cand be adjusted so that the focal point of the beam will change corresponding to the position of the reticle 42 within the image V of the eye E within the telescope 10.

In another embodiment, the reticle 42 can be substituted by a stereo target system by having dots in the oculars.

We claim:

1. An ophthalmic microscope combined with a laser coagulator and a binocular, a first telescope tubular section connected to the binocular, a second tubular section slideably connected to the first section, the second section comprising an objective lens and a first reticle fixed to the second telescope section spaced within the telescope, a second reticle means provided on the first telescopic section between the objective lens and the first reticle, a field lens within the first telescopic section and arranged such that the focal point of the field lens coincides with the second reticle, illumination means adjacent to the field lens and having a focal point coincident with the second reticle, laser means including means on the first telescopic section for passing an unfocused laser beam into the telescope along an axis contained within the plane which includes the second reticle, a reflecting mirror provided in the telescope and above the optical axis of the telescope and adapted to deflect the unfocused laser beam towards said objective lens, means for providing an afocal system, means for providing an image of the eye within the telescope and the second reticle can be located in different locations in the image of the eye on adjustment of said second tubular section corresponding with the object target within the eye.

2. A device as defined in claim 1, wherein a portion of an equi-concave lens is provided and mounted to the first telescopic section between the reflecting mirror and the objective lens and is adapted to diverge the unfocused laser beam passing to the objective lens.

3. A device as defined in claim 2, wherein the objective lens is a convex lens adapted to emit the rays therefrom.

4. A binocular for use with a fundus microscope for the purpose of erecting the inverted image and transposing from the left objective to the right eye and from the right objective to the left eye the rays emitting from the fundus microscope, the binocular including a pair of objective lenses placed behind a field lens of a given fundus microscope, the pair of objective lenses being in the same plane at right angles to the optical axis thereof and being adapted to split the rays from the left side and the right side, a first rhomboid prism for diverting the rays emitting from the objective lens on one of the left and right sides and passing these rays to the other of the right and left sides, a second rhomboid prism adjacent the first rhomboid prism and adapted for diverting the rays from one of a left and right side to the other eye thereof.

5. A device as defined in claim 4, wherein said pair of rhomboid prisms are spaced apart and adapted to provide an adjustable distance between the oculars.

6. A device as defined in claim 4, wherein means are provided within the binocular to ensure that the rays pass through an equal distance of prism substance.

7. An ophthalmic microscope combined with a laser coagulator, the microscope including a binocular and a first telescopic tubular section connected to the binocular with a field lens in the tubular section near the binocular, the binocular including a pair of first objective lenses placed behind the field lens, the pair of first objective lenses being in the same plane at right angles to the optical axis of the field lens in the tubular section and being adapted to split the rays from the left side to the right side, a first rhomboid prism for diverting the rays emitting from the objective lens on one of the left and right sides and passing these rays to the other of the right and left sides, and a second rhomboid prism adjacent the first rhomboid prism and adapted to divert the rays from one of a left and right side to the other side thereof; a second tubular section slideably connected to the first telescopic tubular section, the second tubular section comprising an second objective lens and a first reticle fixed to the second tubular section spaced within the telescope, a second reticle means provided on the first telescopic section between the second objective lens and the first reticle, said field lens within the first telescopic tubular section arranged such that the focal point thereof coincides with the second reticle, illumination means adjacent to the field lens and having a focal point coincident with the second reticle, laser means including means on the first telescopic section for passing an unfocused laser beam into the telescope along an axis contained within the plane which includes the second reticle, a reflecting mirror provided in the telescope and above the optical axis of the telescope and adapted to deflect the unfocused laser beam towards said first objective lens, means for providing an afocal system, means for providing an image of the eye within the telescope and the second reticle can be located at different locations in the image of the eye on adjustment of said second tubular section corresponding with the object target within the eye.

* * * * *